(12) United States Patent
McKinley et al.

(10) Patent No.: US 10,190,618 B2
(45) Date of Patent: Jan. 29, 2019

(54) TRACK BOLT

(71) Applicant: Caterpillar Inc., Peoria, IL (US)

(72) Inventors: Timothy Allen McKinley, Peoria, IL (US); Zachary Tyler Donlan, Peoria, IL (US)

(73) Assignee: Caterpillar Inc., Deerfield, IL (US)

( * ) Notice: Subject to any disclaimer, the term of this patent is extended or adjusted under 35 U.S.C. 154(b) by 0 days.

(21) Appl. No.: 15/630,309

(22) Filed: Jun. 22, 2017

(65) Prior Publication Data

US 2018/0372142 A1 Dec. 27, 2018

(51) Int. Cl.
*G01L 5/00* (2006.01)
*F16B 31/02* (2006.01)
*G01L 5/16* (2006.01)
*G01N 29/24* (2006.01)

(52) U.S. Cl.
CPC ............ *F16B 31/02* (2013.01); *G01L 5/0019* (2013.01); *G01L 5/167* (2013.01); *G01N 29/2475* (2013.01)

(58) Field of Classification Search
CPC ...... F16B 31/02; G01L 5/167; G01N 29/2475
USPC .................................................. 73/761, 795
See application file for complete search history.

(56) References Cited

U.S. PATENT DOCUMENTS

| 5,461,923 A | * | 10/1995 | Meisterling | ............. G01L 5/246 73/597 |
| 8,177,464 B2 | * | 5/2012 | Zendehroud | .......... F16B 31/025 411/8 |
| 9,488,212 B2 | | 11/2016 | Hsieh | |
| 2012/0146399 A1 | * | 6/2012 | Nebergall | .......... B62D 55/0882 305/108 |

FOREIGN PATENT DOCUMENTS

| CN | 203097917 | 7/2013 |
| JP | 2009053050 | 3/2009 |
| WO | 2010089052 | 8/2010 |

* cited by examiner

*Primary Examiner* — Max Noori
(74) *Attorney, Agent, or Firm* — Bookoff McAndrews

(57) ABSTRACT

A track bolt for an undercarriage system includes a head portion. The track bolt also includes a body portion extending from the head portion. The track bolt further includes a piezo ceramic sensor mounted in a counter bore provided in the track bolt. The piezo ceramic sensor measures a value of track bolt elongation such that the value of the track bolt elongation is used to calculate a clamping force in the track bolt. The track bolt includes a plug member disposed in the counter bore for sealing the piezo ceramic sensor.

20 Claims, 5 Drawing Sheets

TRACK BOLT

TECHNICAL FIELD

The present disclosure relates to a track bolt associated with an undercarriage system of a machine.

BACKGROUND

Tracked machines, such as tractors and excavators, include an undercarriage system for propelling the machines on ground. The undercarriage system includes track links that are coupled to track shoes. The track shoes are embodied as ground contacting members. Each track link is coupled with the respective track shoe by a pair of track bolts. During initial coupling, the track bolts are tightened under a certain amount of clamping force so that the track bolts do not loosen during machine operation. However, the track bolts have a tendency to elongate over time, resulting in loss of clamping force. The loss in clamping force affects stress in a bolted joint between the track link and track shoe, which is not desirable. Thus, the track bolts are periodically checked for elongation and thereby the clamping forces.

U.S. Pat. No. 9,488,212 describes a dust proof structure for a stress-sensible screw is provided. The dust proof structure includes a sensing screw, a head, a dust proof boot and a displayer. The sensing screw includes a base and at least one exposed lead, and the exposed lead is located in the base and transmits a stress signal. The head includes a lead base, the head is fitted with the base, and the exposed lead is detachably connected to the lead base. The dust proof boot is disposed on the head, and sleeves a connecting portion between the lead base and the exposed lead. The displayer is electrically connected with the head for displaying the stress signal.

SUMMARY OF THE DISCLOSURE

In one aspect of the present disclosure, a track bolt for an undercarriage system is provided. The track bolt includes a head portion. The track bolt also includes a body portion extending from the head portion. The track bolt further includes a piezo ceramic sensor mounted in a counter bore provided in the track bolt. The piezo ceramic sensor measures a value of track bolt elongation such that the value of the track bolt elongation is used to calculate a clamping force in the track bolt. The track bolt includes a plug member disposed in the counter bore for sealing the piezo ceramic sensor.

In another aspect of the present disclosure, an undercarriage joint is provided. The undercarriage joint includes a track shoe adapted to contact a ground surface. The undercarriage joint also includes a track link for coupling with the track shoe. The undercarriage joint further includes a track bolt for coupling the track link with the track shoe. The track bolt includes a head portion. The track bolt also includes a body portion extending from the head portion. The track bolt further includes a piezo ceramic sensor mounted in a counter bore provided in the track bolt. The piezo ceramic sensor measures a value of track bolt elongation such that the value of the track bolt elongation is used to calculate a clamping force in the track bolt. The track bolt includes a plug member disposed in the counter bore for sealing the piezo ceramic sensor.

In yet another aspect of the present disclosure, a method of measuring clamping force in a track bolt of an undercarriage system is provided. The method includes mounting a piezo ceramic sensor in a counter bore provided in the track bolt. The method also includes measuring a value of track bolt elongation ultrasonically using the piezo ceramic sensor. The method further includes calculating the clamping force in the track bolt based on the measured value of the track bolt elongation.

Other features and aspects of this disclosure will be apparent from the following description and the accompanying drawings.

DETAILED DESCRIPTION

Wherever possible, the same reference numbers will be used throughout the drawings to refer to the same or the like parts. Also, corresponding or similar reference numbers will be used throughout the drawings to refer to the same or corresponding parts.

Figure 1:
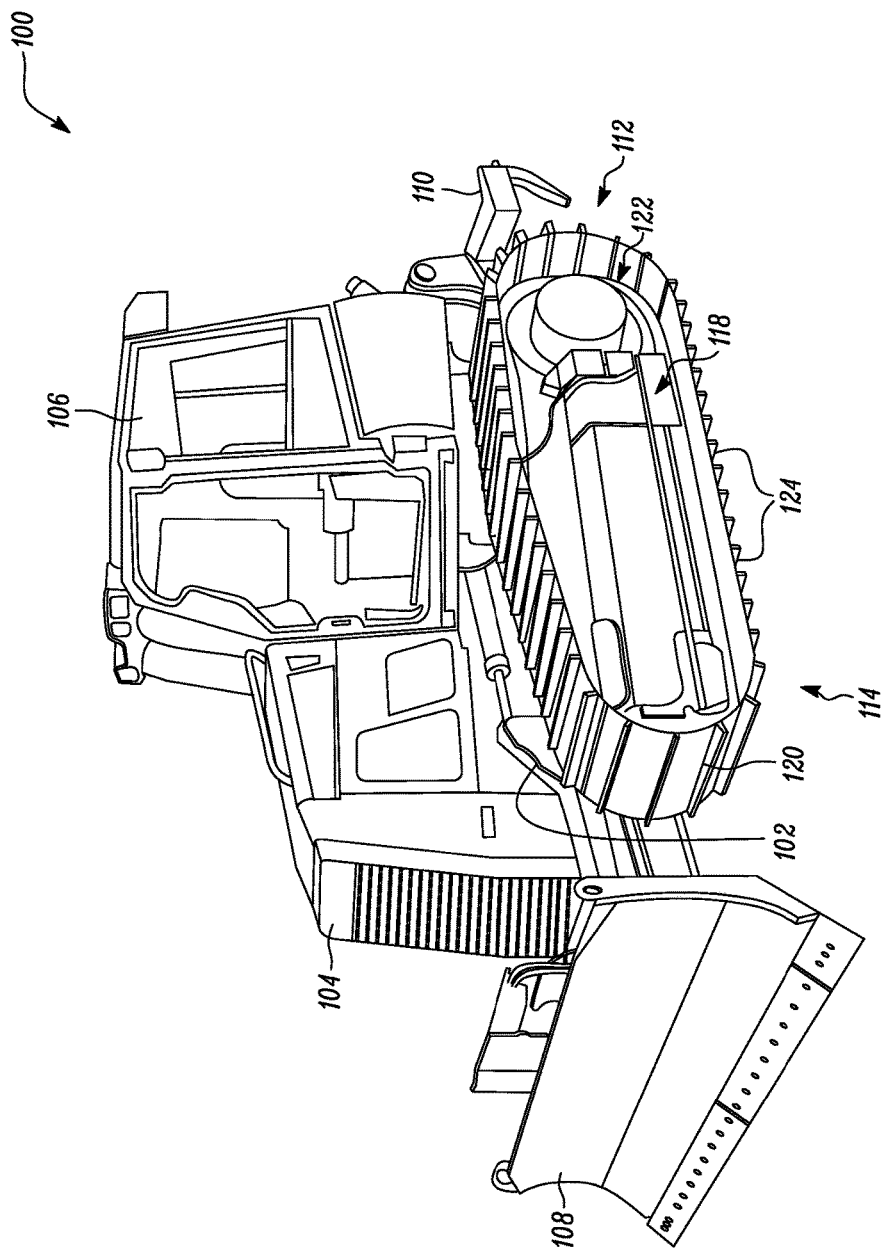
FIG. 1 is a perspective view of an exemplary machine having an undercarriage system, according to one embodiment of the present disclosure.

FIG. 1 is a perspective view of a machine 100, according to one embodiment of the present disclosure. In the illustrated embodiment, the machine 100 is embodied as a track type tractor. Alternatively, the machine 100 may embody any other tracked machine known in the art, such as a tracked excavator. Further, the machine 100 can operate at a worksite, such as, a mine, a landfill, a quarry, a construction site, and the like. The machine 100 may perform operations associated with an industry such as mining, construction, farming, transportation, or any other industry known in the art.

The machine 100 includes a chassis 102. The machine 100 also includes an engine (not shown) mounting in an engine enclosure 104 at a front end of the machine 100 for providing propulsion power to the machine 100. The engine may be an internal combustion engine, such as a compression ignition diesel engine, without any limitations. A cab 106 is mounted to the chassis 102. When the machine 100 is embodied as a manual or a semi-autonomous machine 100, an operator of the machine 100 is seated within the cab 106 to perform one or more machine operations. The machine 100 also includes work implements 108, 110 to perform one or more work operations. The machine 100 illustrated herein includes two work implements 108, 110 mounted at the front end and a rear end of the machine 100, respectively.

Further, the chassis 102 is supported on an undercarriage system 112. The undercarriage system 112 allows propulsion of the machine 100. The undercarriage system 112 includes a pair of track assemblies, provided on either sides of the machine 100. The track assembly 114 mounted on a left side of the machine 100 is shown in the accompanying figure. The track assembly 114 and its components will now be explained with reference to FIG. 1, and it should be noted that the details of the track assembly 114 provided below is equally applicable to the track assembly mounted on a right side of the machine 100. The track assembly 114 includes a track roller frame 118 and an endless track 120. The track assembly 114 further includes various guiding components (not shown) connected to the track roller frame 118. The track 120 engages with the guiding components in order to propel the machine 100 on a ground surface.

Figure 2:
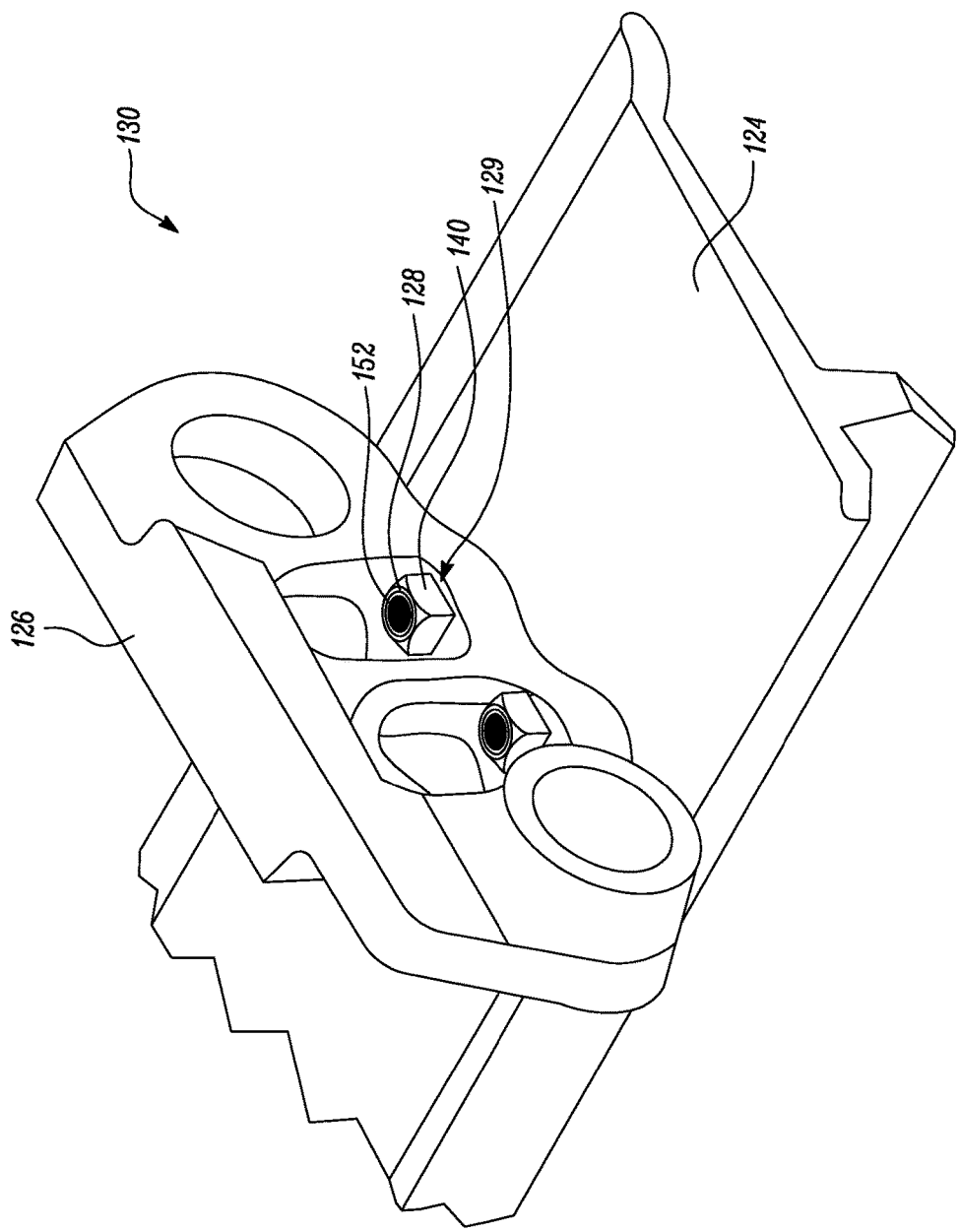
FIG. 2 is a perspective view of an undercarriage joint associated with the undercarriage system of FIG. 1.

Further, the track assembly 114 includes a link assembly 122 that forms a flexible backbone of the track 120 and a number of track shoes 124 coupled to the link assembly 122. The track shoes 124 contacts and engages with the ground surface as the machine 100 moves on the ground surface. The link assembly 122 further includes a number of track links 126 (one of which is shown in FIG. 2) that are connected to one another at pivot joints. Further, a pair of track links 126 is coupled to an associated track shoe 124 by a bolted joint 129. More particularly, each of the track links 126 is coupled with the respective track shoe 124 by a pair of track bolts 128.

FIG. 2 is a perspective view of an undercarriage joint 130 illustrating the track link 126 coupled to the track shoe 124 by the pair of track bolts 128. Each of the track link 126 and the track shoe 124 includes apertures (not shown) that are aligned to receive the track bolts 128. For explanatory purposes, the track bolt 128 will now be explained in detail with reference to FIGS. 2 and 3. However, it should be noted that the details of the track bolt 128 provided below is applicable to each track bolt of the undercarriage system 112, without any limitations.

Figure 3:
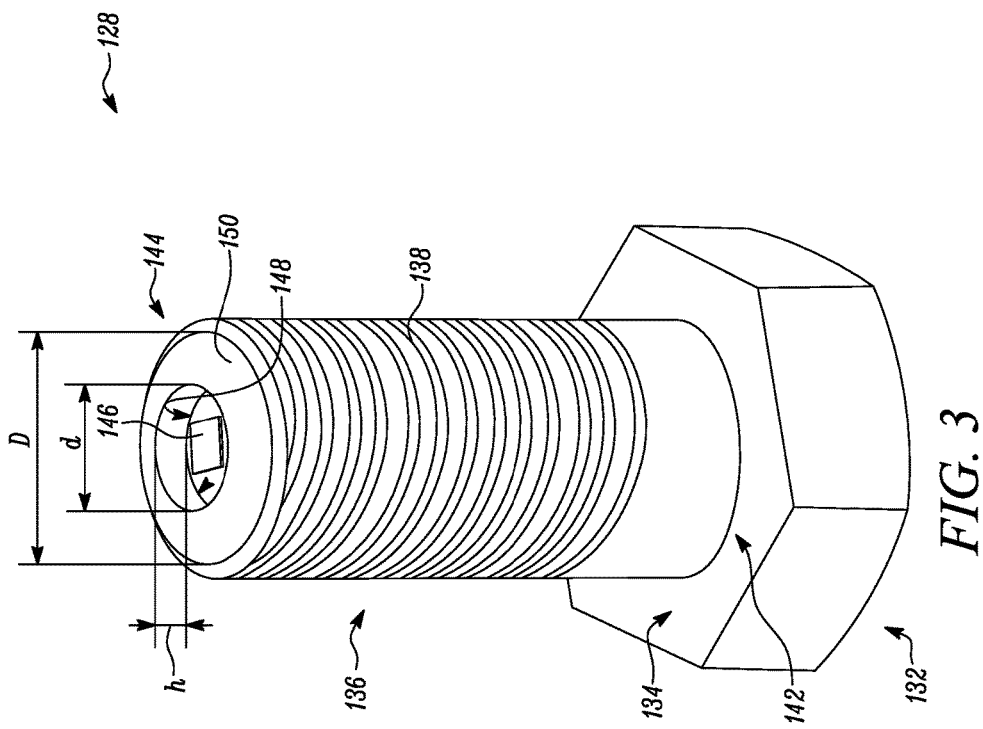
FIG. 3 is a perspective view of a track bolt associated with the undercarriage system, according to one embodiment of the present disclosure.

Referring to FIG. 3, a perspective view of the track bolt 128 is shown. The track bolt 128 includes a head portion 132. The head portion 132 is embodied as a hexagonal head portion, without any limitations. When the track link 126 is coupled to the track shoe 124, a bottom surface 134 of the head portion 132 is in contact with a bottom surface (not shown) of the track shoe 124. Further, the track bolt 128 includes a body portion 136. The body portion 136 extends from the head portion 132, such that a height of the body portion 136 is greater than a height of the head portion 132. A diameter "D" of the body portion 136 is concentric with a diameter of the head portion 132. The body portion 136 may include a number of threads 138 for threadably coupling the track bolt 128 with the track shoe 124 and the track link 126, respectively. The threads 138 also couple with a nut 140 (shown in FIG. 2) for tightening the bolted joint 129. The body portion 136 includes an upper end 142 and a lower end 144. The upper end 142 is integral with the head portion 132 and is in contact with the bottom surface 134 of the head portion 132.

The track bolt 128 also includes a piezo ceramic sensor 146. The piezo ceramic sensor 146 is mounted in a counter bore 148 provided in the track bolt 128. In the embodiment illustrated in FIG. 3, the counter bore 148 is provided within the body portion 136 of the track bolt 128. More particularly, the counter bore 148 is provided at the lower end 144 of the body portion 136, such that the counter bore 148 is in communication with a bottom surface 150 of the body portion 136.

A diameter "d" of the counter bore 148 is concentric with the diameter "D" of the body portion 136. In one example, the diameter "d" of the counter bore 148 may lie in a range between 3 mm to 6 mm, without any limitations. For example, the diameter "d" of the counter bore 148 may be approximately equal to 4 mm. Further, a depth "h" of the counter bore 148 is defined along an axis of extension of the body portion 136. The depth "h" of the counter bore 148 may lie in a range between 4 mm to 10 mm, without any limitations. The diameter "d" and the depth "h" of the counter bore 148 are decided based on dimensions of the track bolt 128 and dimensions of the piezo ceramic sensor 146. It should be noted that the values of the diameter "d" and the depth "h" mentioned herein are exemplary and may vary, based on application requirements.

Further, the piezo ceramic sensor 146 disclosed herein is used for measuring a value of track bolt elongation. More particularly, the piezo ceramic sensor 146, in conjunction with an external reader (not shown), is used to ultrasonically measure the value of the track bolt elongation. The external reader is embodied as an ultrasonic reader having a probe and a display unit, among other components. The value of the track bolt elongation received from the external reader is used to calculate a clamping force in the track bolt 128. The clamping force can be calculated using the following equation:

$$F = \Delta L * k \qquad \text{equation I}$$

Where, F is the clamping force, $\Delta L$ is the track bolt elongation, and k is bolt coefficient.

Further, the clamping force is used to calculate stresses in the bolted joint 129 to ensure that the bolted joint 129 is operating at a desired stress. The stress in the bolted joint 129 can be calculated using the following equation:

$$S = \frac{F}{A} \qquad \text{equation II}$$

Where, S is the stress in the bolted joint 129, F is the clamping force, and A is tensile stress area of the body portion 136 having diameter "D".

It should be noted that the value of the track bolt elongation can be measured at periodic intervals. For example, the value of the track bolt elongation, and eventually the clamping force and the stress in the bolted joint 129 can be first calculated when the track link 126 is coupled with the track shoe 124. Henceforth, the value of the track bolt elongation, and eventually the clamping force and the stress can be calculated during servicing or maintenance of the machine 100 to check if the track bolt 128 is retaining its clamping force over a period of time and field usage.

The track bolt 128 also includes a plug member 152 (shown in FIG. 2). The plug member 152 is disposed in the counter bore 148 after the piezo ceramic sensor 146 is mounted in the counter bore 148. The plug member 152 seals the piezo ceramic sensor 146 within the counter bore 148. The plug member 152 inhibits debris or other foreign materials to enter the counter bore 148 and contact the piezo ceramic sensor 146, thereby protecting the piezo ceramic sensor 146. Further, the plug member 152 is made of a material that is piercable by the probe of the external reader, thereby allowing the probe to penetrate the plug member 152 and contact the piezo ceramic sensor 146. The plug member 152 may be made of a flexible material. In one example, the plug member 152 may be made of curable rubber or silicone. Alternatively, the plug member 152 may be made of any other material that provides protection to the piezo ceramic sensor 146 and allows the probe to penetrate therethrough, without limiting the scope of the present disclosure.

Figure 4:
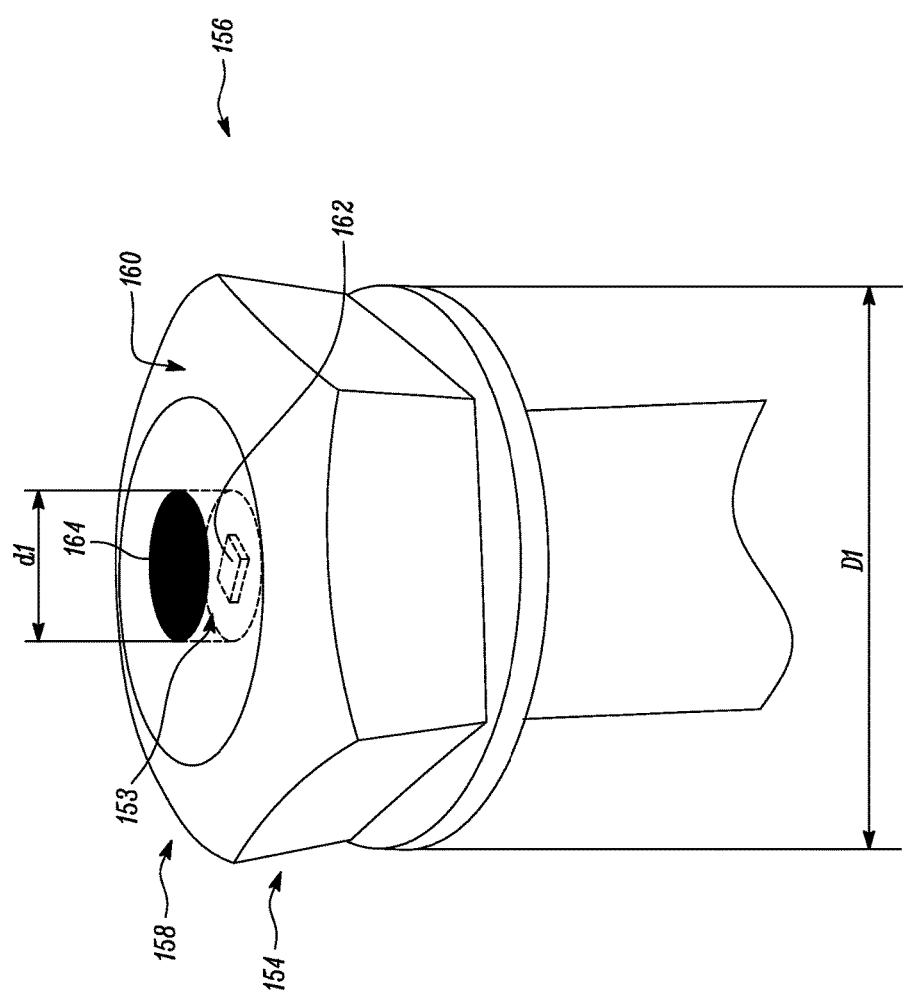
FIG. 4 is a perspective view of a track bolt associated with the undercarriage system, according to another embodiment of the present disclosure.

FIG. 4 illustrates another embodiment of the present disclosure. In this embodiment, the counter bore 153 is provided in the head portion 154 of the track bolt 156. More particularly, the counter bore 153 is provided at an upper end 158 of the head portion 154, such that the counter bore 153 is in communication with an upper surface 160 of the head portion 154. The head portion 154 is similar to the head portion 132 explained with reference to FIG. 3.

A diameter "d1" of the counter bore 153 is concentric with a diameter "D1" of the head portion 154. Further, the piezo ceramic sensor 162 and the plug member 164 are mounted in the counter bore 153 that is provided within the head portion 154 of the track bolt 156. It should be noted that the piezo ceramic sensor 162 and the plug member 164 disclosed herein is similar to the piezo ceramic sensor 146 and the plug member 152 explained with reference to FIGS. 2 and 3.

In one example, the counter bore 148, 153 can be provided in the body portion 136 and the head portion 154 respectively, by machining the body portion 136 and the head portion 154. Alternatively, the track bolt 128, 156 may be molded, casted, or 3D printed, such that the body portion 136 and the head portion 154 includes the counter bore 148, 153 respectively.

INDUSTRIAL APPLICABILITY

The present disclosure relates to the track bolts 128, 156 associated with the undercarriage system 112. The track bolts 128, 156 in conjunction with the external reader provide an easy assessment technique to measure the elongation in the track bolts 128, 156. The track bolts 128, 156 allow maintenance personnel to calculate the clamping force and the stresses in the bolted joint 129 of the undercarriage system 112 using the value of the track bolt elongation. This gives an idea to the maintenance personnel regarding a current condition of the track bolts 128, 156 and also regarding its expected service life. Thus, the maintenance personnel may replace or service the track bolts 128, 156 accordingly, thereby reducing any machine downtime due to failure of the track bolts 128, 156 during field usage.

The track bolts 128, 156 disclosed herein are simple to design and manufacture, and are cost effective. Further, the counter bores 148, 153 provided in the respective track bolts 128, 156 are minor and benign, and do not have any effect on the clamping force or the stresses in the track bolts 128, 156. As the track bolts 128, 156 undergo minimal design modifications to include the piezo ceramic sensor 146, 162, the piezo ceramic sensor 146, 162 can be provided in an existing track bolt. Further, the track bolts 128, 156 can be easily retrofitted on an existing machine 100 in field by customers of the machine 100.

Figure 5:
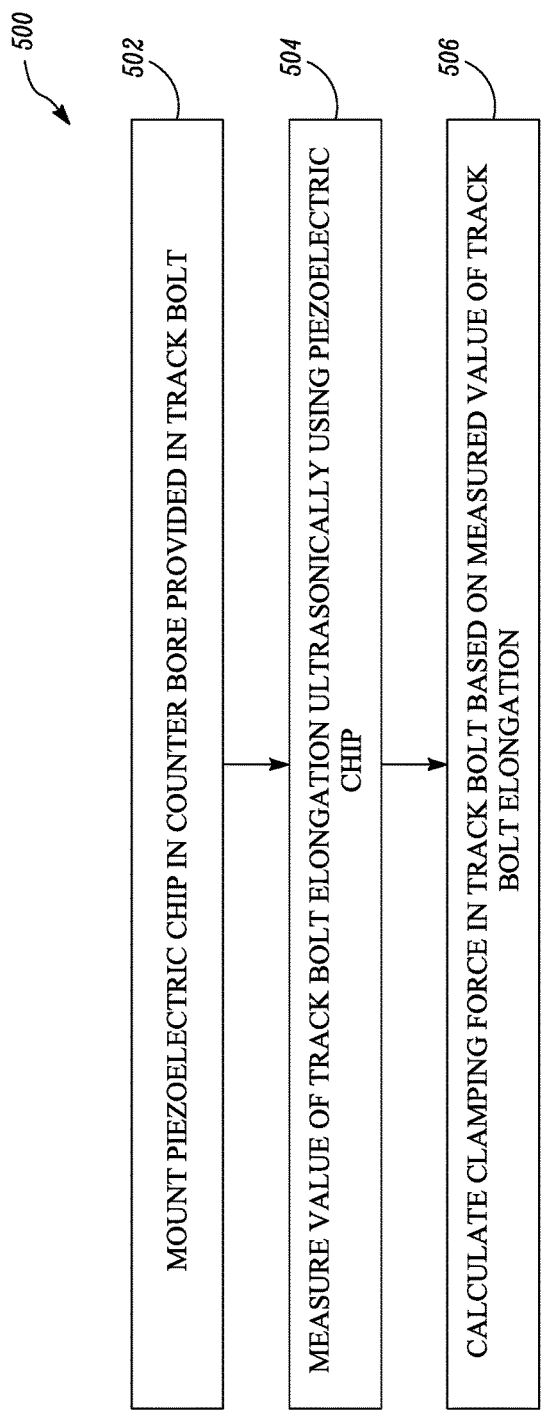
FIG. 5 is a flowchart for a method of measuring clamping force in the track bolt.

FIG. 5 is a flowchart for a method 500 of measuring the clamping force in the track bolts 128, 156 of the undercarriage system 112. At step 502, the piezo ceramic sensor 146, 162 is mounted in the counter bore 148, 153 provided in the respective track bolt 128, 156. In one example, the counter bore 148 is provided within the body portion 136 of the track bolt 128 (see FIGS. 2 and 3). In another example, the counter bore 153 is provided within the head portion 154 of the track bolt 156 (see FIG. 4). At step 504, the value of the track bolt elongation is measured ultrasonically using the piezo ceramic sensor 146, 162. At step 506, the clamping force in the track bolts 128, 156 is calculated based on the measured value of the track bolt elongation.

Further, the plug member 152, 164 is disposed in the counter bore 148, 153 for sealing and protecting the piezo ceramic sensor 146, 162. The plug member 152, 164 inhibits the debris and other foreign material to enter the counter bore 148, 153 of the respective track bolt 128, 156. The track bolts 128, 156 having the piezo ceramic sensor 146, 162 therefore have high chances of surviving in severe operating environments as the piezo ceramic sensor 146, 162 is protected by the plug member 152, 164. Further, the plug member 152, 164 is made of a material that is piercable by the probe of the external reader, thereby allowing the probe to contact the piezo ceramic sensor 146, 162 by penetrating the plug member 152, 164 with minimal effort.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

The invention claimed is:

1. A track bolt for an undercarriage system, the track bolt comprising:
   a head portion;
   a body portion extending from the head portion;
   a piezo ceramic sensor mounted in a counter bore provided in the track bolt, wherein the piezo ceramic sensor measures a value of a track bolt elongation such that the value of the track bolt elongation is used to calculate a clamping force in the track bolt; and
   a plug member disposed in the counter bore, wherein the plug member is configured to seal the piezo ceramic sensor and to allow a probe of a reader to access the piezo ceramic sensor.

2. The track bolt of claim 1, wherein the track bolt elongation is measured ultrasonically in conjunction with the piezo ceramic sensor.

3. The track bolt of claim 1, wherein the counter bore is concentric with each of the body portion and the head portion.

4. The track bolt of claim 1, wherein the counter bore is provided within the body portion.

5. The track bolt of claim 1, wherein the counter bore is provided within the head portion.

6. The track bolt of claim 1, wherein the plug member inhibits debris from entering the counter bore of the track bolt and wherein the plug member is made of a flexible material that is piercable by the probe of the reader to allow the probe to penetrate the plug member and contact the piezo ceramic sensor.

7. The track bolt of claim 6, wherein the plug member is made of at least one of curable rubber or silicone.

8. The track bolt of claim 1, wherein the track bolt couples a track link of the undercarriage system with a track shoe of the undercarriage system.

9. An undercarriage joint comprising:
   a track shoe adapted to contact a ground surface;
   a track link for coupling with the track shoe; and
   a track bolt for coupling the track link with the track shoe, wherein the track bolt comprises:
      a head portion;
      a body portion extending from the head portion;
      a piezo ceramic sensor mounted in a counter bore provided in the track bolt, wherein the piezo ceramic sensor measures a value of a track bolt elongation such that the value of the track bolt elongation is used to calculate a clamping force in the track bolt; and
      a plug member disposed in the counter bore for sealing the piezo ceramic sensor, wherein the plug member is formed of a flexible material wherein the plug member is made of a material that is piercable by a probe of a reader to allow the probe to penetrate the plug member and to contact the piezo ceramic sensor.

10. The undercarriage joint of claim 9, wherein the track bolt elongation is measured ultrasonically in conjunction with the piezo ceramic sensor.

11. The undercarriage joint of claim 9, wherein the counter bore is concentric with each of the body portion and the head portion.

12. The undercarriage joint of claim 9, wherein the counter bore is provided within the body portion.

13. The undercarriage joint of claim 9, wherein the counter bore is provided within the head portion.

14. The undercarriage joint of claim 9, wherein the plug member inhibits debris from entering the counter bore of the track bolt.

15. The undercarriage joint of claim 14, wherein the plug member is made of at least one of curable rubber or silicone.

16. A method of measuring a clamping force in a track bolt of an undercarriage system, the method comprising:
mounting a piezo ceramic sensor in a counter bore provided in the track bolt;
disposing a plug member in the counter bore for sealing the piezo ceramic sensor;
piercing the plug member with a probe of a reader;
measuring a value of a track bolt elongation ultrasonically using the reader in contact with the piezo ceramic sensor; and
calculating the clamping force in the track bolt based on the measured value of the track bolt elongation.

17. The method of claim 16, further including providing the counter bore within at least one of a body portion of the track bolt or a head portion of the track bolt.

18. The method of claim 16, further including inhibiting debris from entering the counter bore of the track bolt by the plug member.

19. The track bolt of claim 1, wherein the plug member is made of at least one of curable rubber or silicone.

20. The method of claim 16, wherein the plug member is formed of a flexible material that is piercable by the probe of the reader to allow the probe to penetrate the plug member and contact the piezo ceramic sensor.

* * * * *